(12) United States Patent
Schumann

(10) Patent No.: US 6,949,874 B2
(45) Date of Patent: Sep. 27, 2005

(54) ELECTRODE SYSTEM

(75) Inventor: Bernd Schumann, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 392 days.

(21) Appl. No.: 10/153,316

(22) Filed: May 22, 2002

(65) Prior Publication Data
US 2002/0195340 A1 Dec. 26, 2002

(30) Foreign Application Priority Data
May 22, 2001 (DE) .......................... 101 24 907

(51) Int. Cl.[7] .............................................. H01J 1/02
(52) U.S. Cl. ...................... 313/358; 73/23.31; 422/98; 436/151
(58) Field of Search .......................... 73/23.31, 23.33, 73/31.05, 204, 426–431, 433, 434; 422/90, 98; 436/145, 151; 313/346 D, 275, 15, 358

(56) References Cited

U.S. PATENT DOCUMENTS

| 3,075,114 | A | * | 1/1963 | Germeshausen | ............. 313/42 |
|---|---|---|---|---|---|
| 3,932,246 | A | * | 1/1976 | Stadler et al. | ........... 156/89.11 |
| 4,007,435 | A | * | 2/1977 | Tien | ............................. 338/34 |
| 4,028,642 | A | * | 6/1977 | Kushida et al. | ............. 323/366 |
| 4,405,878 | A | * | 9/1983 | Oliver | .................... 313/346 R |
| 4,656,832 | A | * | 4/1987 | Yukihisa et al. | .............. 60/303 |
| 5,134,080 | A | | 7/1992 | Bell et al. | |
| 5,708,585 | A | * | 1/1998 | Kushion | ..................... 701/108 |
| 5,996,337 | A | * | 12/1999 | Blosser et al. | ................ 60/274 |
| 6,238,536 | B1 | * | 5/2001 | Lundgren et al. | ........... 204/426 |
| 6,689,322 | B2 | * | 2/2004 | Mills et al. | .................... 422/98 |

FOREIGN PATENT DOCUMENTS

| DE | 219 587 | 3/1985 |
|---|---|---|
| DE | 198 53 841 | 4/2001 |
| EP | 1 048 948 | 11/2000 |

* cited by examiner

Primary Examiner—Vip Patel
Assistant Examiner—Glenn Zimmerman
(74) Attorney, Agent, or Firm—Kenyon & Kenyon

(57) ABSTRACT

An electrode system, particularly for installation in an exhaust line, has a holding body made of an insulating material, on which at least one operating electrode is positioned. The holding body has a heating device for facilitating easy cleaning in the installed position.

10 Claims, 5 Drawing Sheets

ELECTRODE SYSTEM

FIELD OF THE INVENTION

The present invention relates to an electrode system, particularly for installation in an exhaust line, and a method for cleaning an electrode system.

BACKGROUND INFORMATION

An electrode system of the type initially described may be implemented, for example, as a carbon black sensor which may be used for installation in an exhaust system of a diesel engine.

A conventional electrode system may be constructed in such a manner that it includes a holding body made of a ceramic material, on which at least one operating electrode is positioned, which may be used, for example, for induction measurements of charged particles of exhaust of a diesel engine. The holding body may penetrate a socket, which may be implemented as a socket of a spark plug. The socket may be screwed into a corresponding thread which may be implemented in a wall of a pipe of an exhaust system. The electrode bushing may be connectable, at a region lying outside the pipe, to an analysis and/or control device via appropriately designed terminals.

Furthermore, particles such as carbon black particles may be capable of being electrically charged using an electrode. The charge of the particles may then be given off again at an electrode having a suitable polarity and/or a suitable shape, such as that of a Faraday cup. It may be required to use electrodes which are sufficiently well insulated.

It may be required, particularly if an electrode system of the type initially described is used continuously in a pipe of an exhaust system, to maintain the insulation resistance of the holding body between the electrode and the pipe and therefore to check it regularly using an electrical measurement. The electrically charged particles may precipitate on the holding body and thus may reduce its insulation resistance.

For this reason, it may be required to clean the holding body, which cleaning is conventionally performed in a chemical or mechanical manner.

SUMMARY OF THE INVENTION

An electrode system according to the present invention provides a holding body implemented with a heating device so that it may be cleaned easily in the installed position.

In an electrode system according to the present invention, it may be only required to activate the heating device, so that particles, such as carbon black particles, which may have precipitated in a holding body projecting into a testing or measuring volume, may be combusted.

The heating device may also be kept at a temperature level at which no particles may accumulate on the holding body.

An electrode system according to the present invention may be suitable for installation in an exhaust system of a motor vehicle having a diesel engine. However, it may also, for example, be used in other types of exhaust lines, for example those of an oil heater.

The operating electrode may be used, for example, for measuring the carbon black concentration in exhaust of a diesel engine.

The heating device itself may be shielded against particles that may precipitate on the electrode system so that its efficiency may not be impaired by these particles. For example, the heating device may be embedded in the holding body, which may be manufactured from a ceramic.

Alternatively, the heating device may be positioned in a hollow space of the holding body which is open on a side lying outside the testing and/or measuring volume. The heating device may be inserted into the holding body from this side.

The holding body may, for example, be implemented in a rod or tube shape and may have an essentially rectangular, round, or otherwise suitable cross section.

An exemplary embodiment of the electrode system according to the present invention may include a device for measuring an insulation resistance of the holding body. A device of this type, which may be configured for measuring an impedance and/or a resistance or a capacitance, may be positioned on or in the holding body inside the testing volume and may be used for detecting particle accumulations on the holding body. Using the measuring device, a point in time may be determined at which the heating device may be activated so that particles precipitated on the holding body break away or at which the temperature of the holding body may be elevated in such a manner that no particles accumulate there.

Through the combination of the heating device and the device for measuring the insulation resistance, accumulations of charged particles on the holding body may be detected and appropriate cleaning steps may then be initiated. A testing and cleaning routine of this type may run automatically.

The device for measuring the impedance may be implemented in such a manner that it includes a testing electrode which is located between a first holding body end, on which the at least one operating electrode is positioned, and an attachment region.

In this manner, it may be ensured that the insulation resistance may be measured in the region of the holding body which lies between the operating electrode and the attachment region, which may be metallic, and which may be attached in the operating state, for example, to a pipe of an exhaust system. The attachment arrangement may be connected to ground.

An electrode system according to the present invention may include a socket for attachment to an exhaust system. The socket, which may be manufactured from metal, may, for example, be implemented as a spark plug socket, so that it may be penetrated by the holding body and may have a thread to be screwed into a corresponding thread of a wall of a pipe.

In an exemplary embodiment, the operating electrode may, for example, include at least one grid which may be used for charging carbon black particles.

In a further exemplary embodiment, the operating electrode may also be implemented in a cup shape. An exemplary embodiment of the operating electrode of this type, which may essentially correspond to a Faraday cup, may be suitable for charge measurement.

The present invention also provides an exemplary method for cleaning an electrode system, which has a holding body made of an insulating material on which at least one operating electrode is implemented. In this exemplary method, particles precipitated on the holding body may be removed by heating the holding body using a heating device. The holding body may, for example, be heated continuously or periodically. The heating device may be operated as a function of the insulation resistance of the holding body, in such a manner that the temperature of the heating device is elevated as the insulation resistance of the holding body falls.

DETAILED DESCRIPTION

Figure 1:
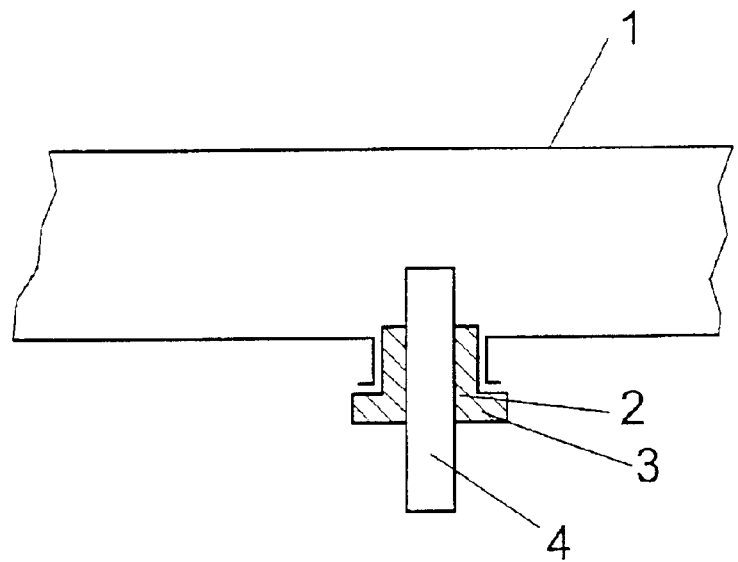
FIG. 1 shows a schematic illustration of a pipe of an exhaust system of a diesel engine having an electrode system according to an exemplary embodiment of the present invention.
Figure 2:
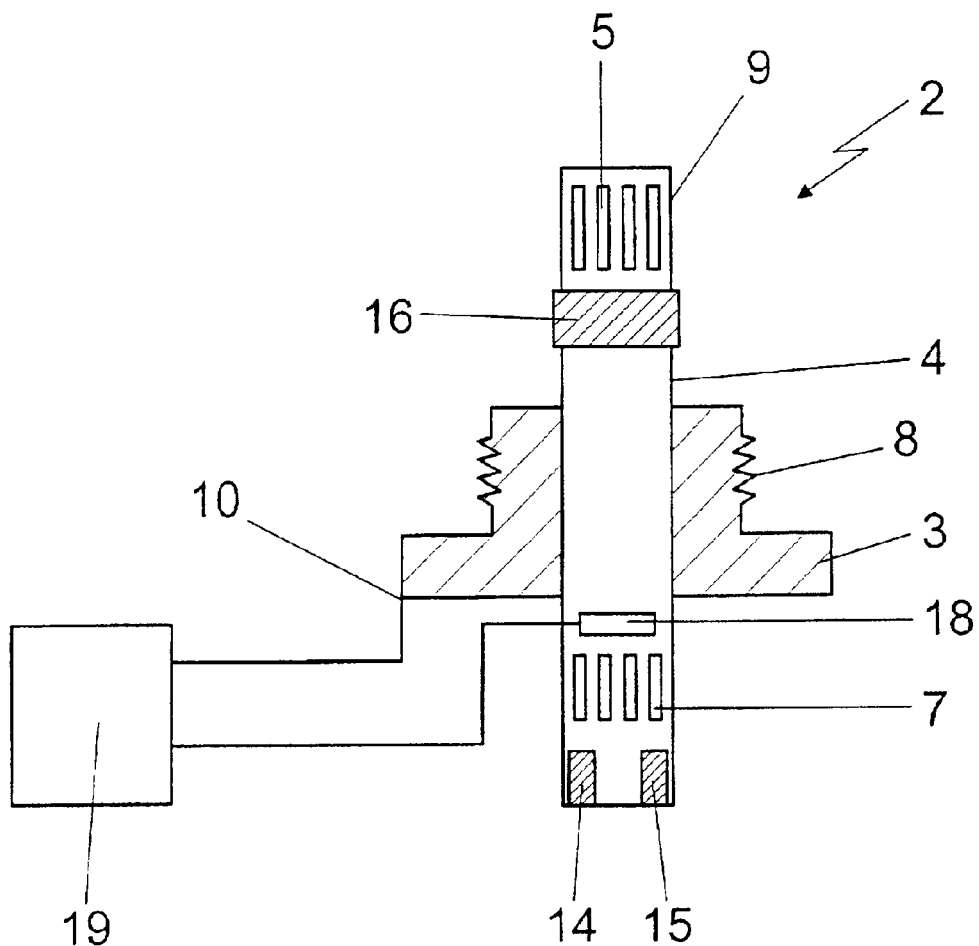
FIG. 2 shows a more detailed schematic illustration of the electrode system shown in FIG. 1.
Figure 3:
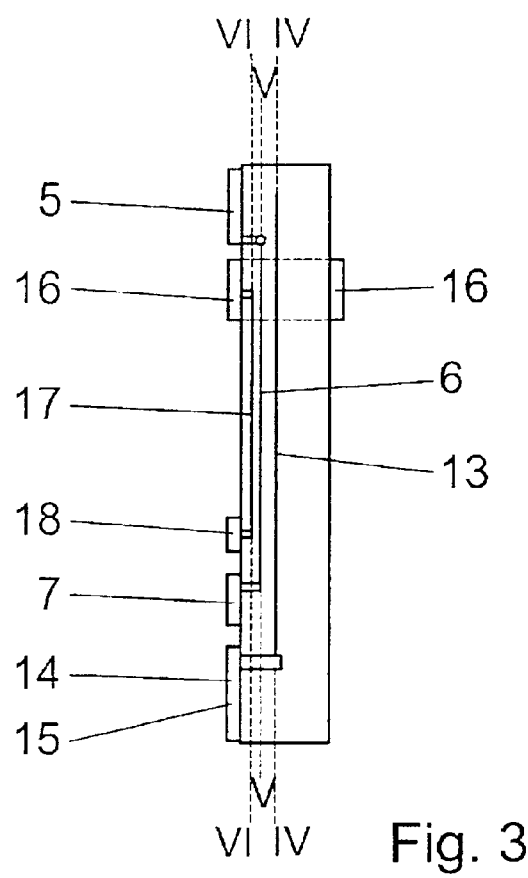
FIG. 3 shows a schematic projection of a holding body of the electrode system shown in FIG. 1.
Figure 4:
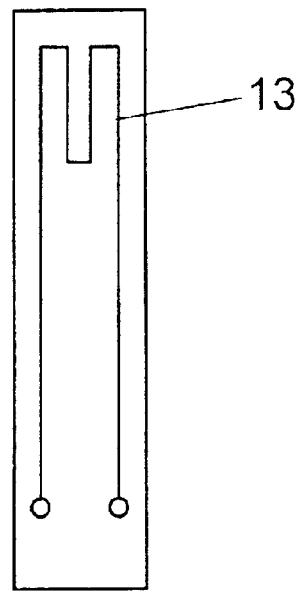
FIG. 4 shows a cross-sectional view of a section through the holding body along line IV—IV in FIG. 3.
Figure 5:
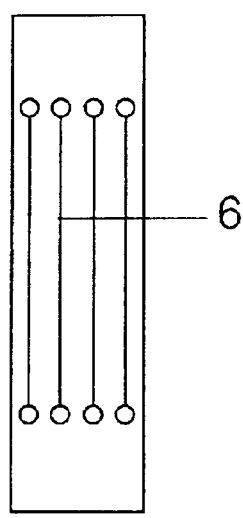
FIG. 5 shows a cross-sectional view of a section through the holding body along line V—V in FIG. 3.
Figure 6:
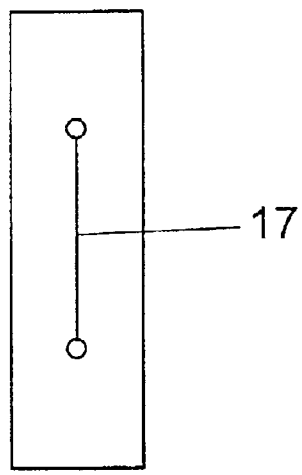
FIG. 6 shows a cross-sectional view of a section through the holding body along line VI—VI in FIG. 3.

In FIG. 1, an exhaust pipe 1 of an exhaust system of a diesel engine is illustrated, into which an electrode system 2 is screwed in the radial direction. Electrode system 2, which is illustrated in more detail in FIGS. 2 to 6, has a socket 3, made of a metallic material, which is implemented having an external thread 8 which engages in a corresponding internal thread of exhaust pipe 1.

Socket 3 is penetrated by a holding body 4, which is made of a ceramic and insulating material. Holding body 4 is essentially rod-shaped in this case and has a rectangular cross-section. One end 9 of holding body 4 projects into exhaust pipe 1.

Four operating electrodes 5 are implemented on end 9 of holding body 4, which are used for measuring carbon black particles in exhaust flowing through exhaust pipe 1. Electrodes 5 are each connected to a terminal 7 via bushings 6 embedded in holding body 4. Electrode terminals 7, of which there are therefore five, are connectable to analysis and/or control electronics.

Furthermore, embedded in ceramic holding body 4 is an essentially axially oriented heating element 13, which is provided with two terminals 14 and 15, which lie outside exhaust pipe 1 and via which heating element 13 is connectable to a voltage source, which is not shown.

Furthermore, a testing electrode 16 is positioned on holding body 4 which is used for measuring the insulation resistance of holding body 4. Testing electrode 16, which surrounds holding body 4, is connected via a bushing 17 to terminal 18, which lies outside exhaust pipe 1. Terminal 18 is in turn connected to a resistance measuring instrument 19, whose second input is connected to a terminal 10 which is implemented on socket 3. Therefore, the insulation resistance of ceramic holding body 4 between testing electrode 16 and socket 3 may be measured using measuring instrument 19.

The insulation resistance of holding body 4 in the region lying between testing electrode 16 and socket 3 may, however, also be determined in a further exemplary embodiment via a capacitance measurement.

Multiple testing electrodes may be used.

Electrode system 2 illustrated in FIGS. 1 to 6 may operate in the manner described in the following.

Operating electrodes 5 of electrode system 2 are used for measuring carbon black particles in exhaust flowing through exhaust pipe 1. The measurement may, for example, be an induction measurement of charged carbon black particles which flow past electrode system 2. If electrically charged particles precipitate in the region of holding body 4 lying between testing electrode 16 and socket 3, the electrical resistance of this region may be reduced. This insulation resistance is measured using measuring instrument 19. As soon as the insulation resistance has fallen below a predefined threshold value, a voltage source connected to heating element 13 via terminals 14 and 15 is activated, so that ceramic holding body 4 is heated, due to which its surface is burned free of the carbon black particles.

Figure 7:
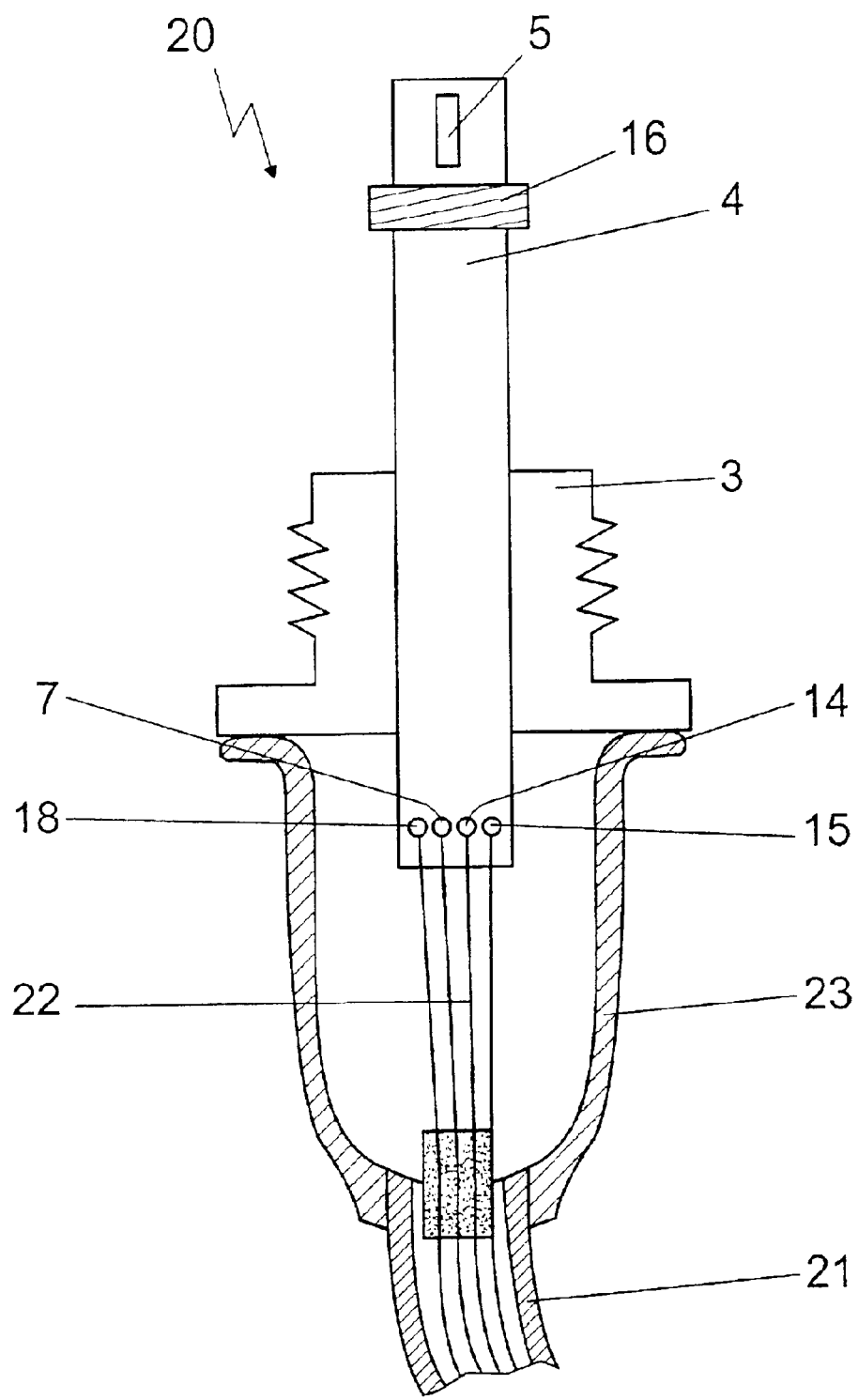
FIG. 7 shows an electrode system having a protective cap.

An alternative exemplary embodiment of an electrode system 20 is illustrated in FIG. 7. The design of electrode system 20 may largely correspond to that of the electrode system shown in FIGS. 1 to 6. Electrode system 20, however, has only one operating electrode 5, which is connected to a terminal 7 via a bushing, which is not shown here.

A testing electrode 16 is connected to a terminal 18, and a heating element embedded in holding body 4 is provided with terminals 14 and 15. Terminal 7 of operating electrode 5, terminal 16 of testing electrode 16, and terminals 14 and 15 of the heating element are each connected to a line 22. Lines 22 are initially guided into a cover cap 23, which forms a tight hermetic seal, and then run into a cable strand 21, which adjoins cover cap 23 on the side facing away from holding body 4. Cable strand 21 leads to an electronic measuring and control device.

Figure 8:
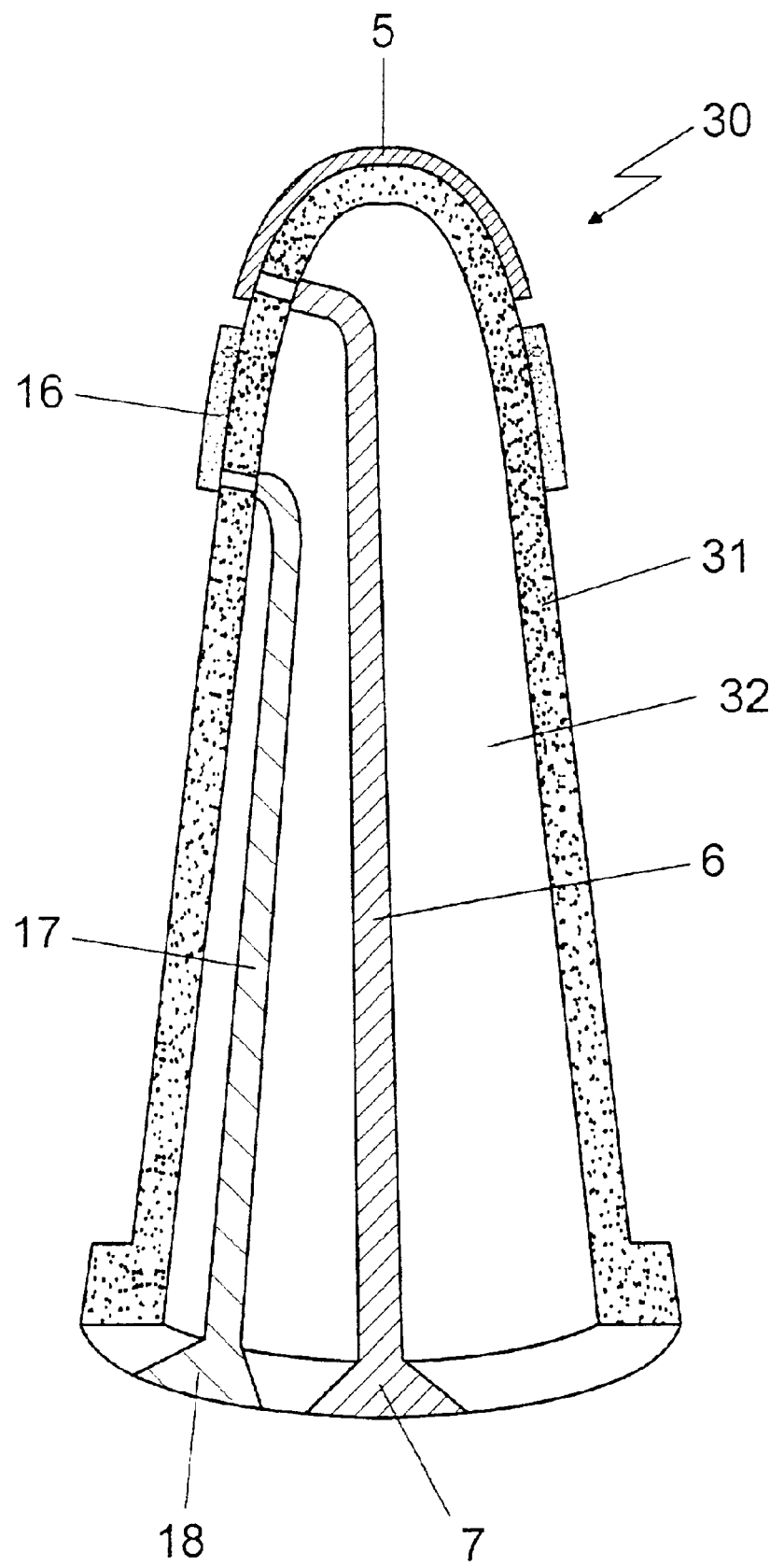
FIG. 8 shows a longitudinal cross-sectional view of an electrode system in the shape of a hollow cone.

In FIG. 8, an electrode system 30 is illustrated which is implemented having a holding body 31 which essentially has the shape of a rounded hollow cone and includes an attachment arrangement for attachment to an exhaust system.

An operating electrode 5, which is connected to a terminal 7, indicated only schematically, for a measurement and/or control device, via a bushing 6, running in holding body 31, which is shaped like a hollow cone, is implemented on the tip of ceramic holding body 31. The attachment arrangement lies on the end of electrode system 30 facing away from operating electrode 5.

In addition, an essentially annular testing electrode 16, which is connected via a bushing 17 in holding body 31, which is shaped like a hollow cone, to a terminal 18, also only shown schematically, for a measuring instrument, is implemented on the circumference of holding body 31, which has a hollow 32.

Furthermore, a heating device for holding body 31 is also positioned inside hollow 32.

Figure 9:
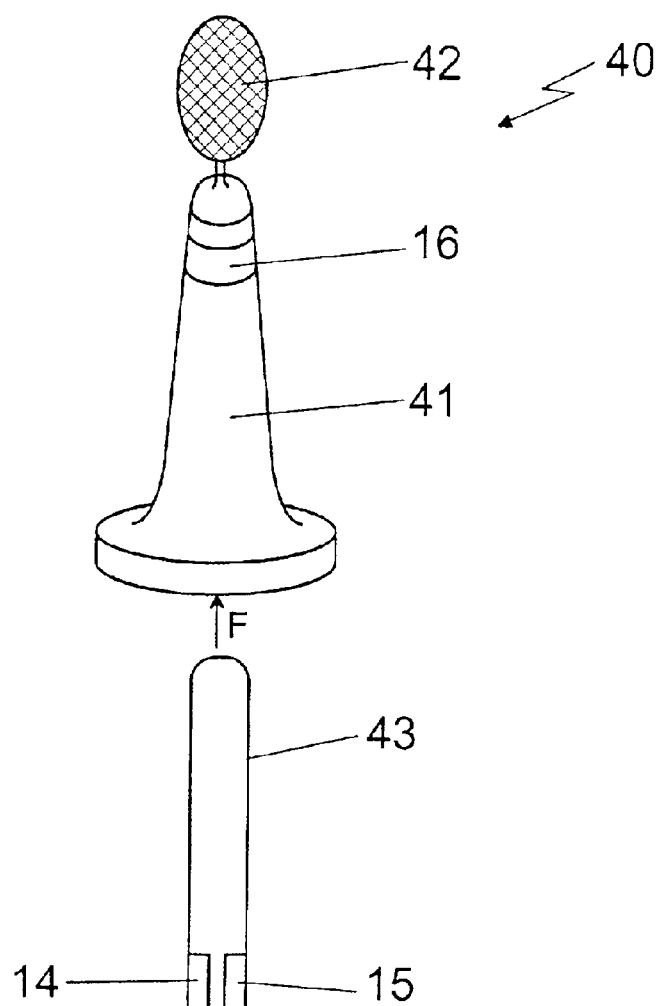
FIG. 9 shows an electrode system in the shape of a hollow cone having a grid electrode.

In FIG. 9, an electrode system 40, whose configuration may essentially correspond to that of the electrode system shown in FIG. 8, is illustrated in simplified form. However, in electrode system 40, a grid-shaped electrode 42 for charging carbon black particles is implemented on the tip of a ceramic holding body 41.

Furthermore, a heating element 43 having two terminals 14 and 15, which is insertable into the hollow of holding body 41, which is shaped like a hollow cone, in the direction of an arrow F and is used for heating holding body 41, is schematically illustrated in FIG. 9.

Figure 10:
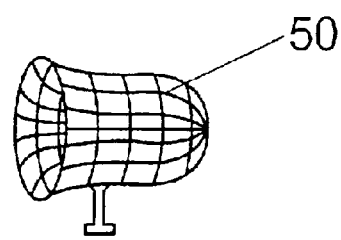
FIG. 10 shows a Faraday cup of an electrode system.

In FIG. 10, a cup-shaped electrode 50 is illustrated which is used as a Faraday cup for charge measurement of carbon black particles and is attachable to a holding body of an electrode system, for example to the holding body shown in FIG. 9, in place of the grid.

The mode of operation of the electrode systems shown in FIGS. 7 to 10 may essentially correspond to that of the electrode system shown in FIGS. 1 to 6.

What is claimed is:

1. An electrode system, comprising:
    at least one operating electrode;
    a holding body having a heating device, the holding body being mad of an insulating material on which the at least one operating electrode is positioned; and
    a device for measuring an insulation resistance of the holding body, wherein the device for measuring the insulation resistance includes at least one testing electrode located between a first holding body end and an attachment region.

2. The electrode system according to claim 1, wherein the electrode system is configured for installation in an exhaust line.

3. The electrode system according to claim 1, wherein the heating device is embedded in the holding body.

4. The electrode system according to claim 1, wherein the heating device is positioned in a hollow of the holding body.

5. The electrode system according to claim 1, further comprising:
    a socket for attachment to an exhaust system branch.

6. The electrode system according to claim 1, wherein the at least one operating electrode includes a grid.

7. The electrode system according to claim 1, wherein the at least one operating electrode is configured in a cup shape.

8. The electrode system according to claim 1, further comprising:
    an arrangement for periodically heating the holding body.

9. The electrode system according to claim 1, further comprising:
    an arrangement for operating the heating device as a function of an insulation resistance of the holding body.

10. The electrode system according to claim 1, further comprising:
    an arrangement for elevating a temperature of the heating device as an insulation resistance of the holding body decreases.

* * * * *

UNITED STATES PATENT AND TRADEMARK OFFICE
CERTIFICATE OF CORRECTION

PATENT NO. : 6,949,874 B2
APPLICATION NO. : 10/153316
DATED : September 27, 2005
INVENTOR(S) : Bernd Schumann Page 1 of 1

It is certified that error appears in the above-identified patent and that said Letters Patent is hereby corrected as shown below:

Column 5, line 15, change "being mad of" to --being made of--

Signed and Sealed this

Third Day of October, 2006

JON W. DUDAS
*Director of the United States Patent and Trademark Office*